(12) United States Patent
Bird et al.

(10) Patent No.: US 6,720,552 B2
(45) Date of Patent: Apr. 13, 2004

(54) REPEATING PULSED MAGNET

(75) Inventors: Mark D. Bird, Tallahassee, FL (US);
Iain R. Dixon, Tallahassee, FL (US);
Yehia Eyssa, Tallahassee, FL (US);
Andrei Gavrilin, Tallahassee, FL (US);
Scott Gundluch, Tallahassee, FL (US)

(73) Assignee: FSU Research Foundation, Inc., Tallahassee, FL (US)

( * ) Notice: Subject to any disclaimer, the term of this patent is extended or adjusted under 35 U.S.C. 154(b) by 56 days.

(21) Appl. No.: 10/273,412

(22) Filed: Oct. 17, 2002

(65) Prior Publication Data

US 2003/0127590 A1 Jul. 10, 2003

Related U.S. Application Data

(60) Provisional application No. 60/329,942, filed on Oct. 17, 2001.

(51) Int. Cl.[7] .................................. H05H 3/02
(52) U.S. Cl. ................. 250/251; 250/390.04; 250/376; 250/377; 376/158; 376/159
(58) Field of Search .................. 324/326, 377; 376/158, 159; 250/251, 390.04

(56) References Cited

U.S. PATENT DOCUMENTS 5,310,705 A * 5/1994 Mitlitsky et al. ........... 505/211
6,054,708 A 4/2000 Shimizu

OTHER PUBLICATIONS

Boenig et al., Design of a 16 kV, 100 kA 2 Hz Power Supply for High–Field, Repetitively Pulsed, Split–Pair Magnets, 12th IEEE International Pulsed Power Conference, Jun. 27–30, 1999, pp. 532–535, vol. 1, U.S.A.

Painter et al., Design of 30 T Split–Pair Pulse Coils for LANSCE, IEEE Transactions on Applied Superconductivity, Mar. 2000, 4 pages, vol. 10, Number 1, IEEE Superconductivity Committee, U.S.A.

* cited by examiner

Primary Examiner—John R. Lee
Assistant Examiner—J J Leybourne
(74) Attorney, Agent, or Firm—Senniger, Powers, Leavitt & Roedel

(57) ABSTRACT

A magnet for use with a neutron scattering apparatus. The neutron scattering apparatus provides an incident beam of neutrons to a sample under analysis. The magnet has first and second body portions of high conductivity material and has a mid-plane portion there between in which the sample under analysis is positioned. The first and second body portions of the coil are electrically connected to each other via the mid-plane portion of the coil between the body portions of the coil. The conductive mid-plane portion has a split that allows neutron scattering through large angles.

21 Claims, 11 Drawing Sheets

REPEATING PULSED MAGNET

This application claims the benefit of Provisional application No. 60/329,942 filed Oct. 17, 2001.

BACKGROUND OF THE INVENTION

The present invention relates generally to magnets for use with a neutron scattering apparatus and, particularly, to a high field repeating pulsed magnet having multiple layers of conductor with aluminum split at its mid-plane to allow neutron scattering through large angles.

Neutron scattering is a valuable tool for probing solids and liquids in many fields, including materials science, medical science, engineering, condensed matter physics, chemistry, biology, and geology. In general, neutron scattering involves probing a sample with thermal neutrons generated in a research reactor or accelerator. A neutron, which is an uncharged magnetic subatomic particle, has a wavelength about equal to the spacing between atoms in molecules. As such, neutrons can produce interference patterns from the atomic lattice of a sample. As an incident beam of neutrons passes through it, the atoms in the sample cause the neutrons to scatter. The scattering pattern reveals detailed information about the sample's atomic structure and dynamics.

Those skilled in the art recognize the need for an apparatus that combines neutron scattering with the ability to analyze materials under high magnetic fields. A powerful magnet surrounding a sample that is targeted by the neutron beam permits investigation into aspects of the sample's structure otherwise undetectable by conventional means. Although various magnets have been proposed, a pulsed magnet is desired for use with a pulsed neutron source to permit researchers to look at, for example, the three-dimensional arrangements of the magnetism in solids at microscopic levels.

As described above, a conventional neutron scattering apparatus sends bursts, pulses, or steady streams of neutrons through a sample. Three-dimensional "maps" of the sample's atomic structure appear as some of the neutrons are scattered by the magnetic elements in the sample. A magnet is desired for subjecting the sample to intense magnetic fields while neutron bombardment takes place. In doing so, the analysis provides additional information about the sample not available from neutron scattering alone. Traditionally, these intense magnetic fields are created by superconducting dc (steady-state) coils. Unfortunately, the upper critical field of today's superconductors is around 25 tesla (T). Hence, superconducting magnets available for neutron scattering are presently limited to 15 T. There are many experiments for which higher fields are desirable. It may be possible to build a superconducting magnet with field strength close to 20 T but the space required for such a system would be inconveniently large. Alternatively, it may be possible to build dc resistive magnets with field intensities in the 30 T range. However, the cost to construct such a system might be prohibitive (e.g. around $40 million). To provide fields above 15 T at reasonable costs, Prof. Motokawa at Tohoku University teaches the use of repetitively pulsed magnets. Other high-field pulsed magnets are flushed with liquid nitrogen between pulses, generally requiring 30 minutes or more between pulses.

Presently available repetitively pulsed magnets face considerable problems in withstanding the stress and heat created by the electrical currents required to generate strong, rapidly firing magnetic pulses. In a single day's operation, a high field repetitively pulsed magnet used in neutron scattering experiments may endure more structural strain cycles from pulses than most traditional high field magnets experience in their operational lifetimes. Conventional dc resistive and superconducting magnets, for example, are only able to operate reliably over about 10,000 repetitions due to the fatigue stress limitations. Higher fields and faster pulse rates are desired for improved resolution. Unfortunately, such improvements lead to even greater stresses on the magnet.

Researchers have proposed the use of a repeating pulsed magnet for providing substantially higher magnetic fields for use in neutron scattering. To date, such magnets fail to provide sufficient field strength and operational life span. In addition, they do not permit large angle or multi-angle scattering capability. Rather, such a magnet limits neutron scattering detection to a single angle relative to the incident beam, i.e., through a beam hole in the magnet.

For these reasons, a cost-effective magnet is desired for use with a neutron scattering apparatus for providing a high magnetic field to samples to study neutron/solid and x-ray/solid interactions and scattering and for permitting multi-angle scattering.

SUMMARY OF THE INVENTION

Among the several objects of this invention may be noted the provision of a magnet for use with a neutron scattering apparatus; the provision of a method for analyzing the atomic structure of a sample with a repeating pulsed magnetic field; and the provision of such magnet and method which are economically feasible and commercially practical.

Briefly described, a magnet for use with a neutron scattering apparatus embodying aspects of the invention includes a conductive coil that has a first body portion and a second body portion of high conductivity material, and a mid-plane portion in which the sample under analysis is positioned. The neutron scattering apparatus provides an incident beam of neutrons to the sample under analysis. The first and second body portions of the coil are electrically connected to each other via the mid-plane portion of the coil, and the mid-plane portion of the coil is a conductive material that is substantially non-interactive with neutrons.

In accordance with another aspect of the invention, a method is provided for analyzing the atomic structure of a sample with a repeating pulsed magnetic field. The method includes positioning the sample within a mid-plane portion of a conductive coil. The conductive coil having a first body portion and a second body portion of high conductivity material that are electrically connected to each other via the mid-plane portion. The method further includes directing a neutron beam through an opening in the mid-plane portion of the conductive coil and toward the sample positioned therein. The method further includes energizing the coil to produce magnetic pulses at a repetition frequency of at least approximately 2 Hz and a peak field of at least approximately 30 T when the magnet is operating.

Alternatively the invention may comprise various other methods and systems. Other objects and advantages will become apparent to those skilled in the art from the detailed description herein read in conjunction with the attached drawings.

BRIEF DESCRIPTION OF THE DRAWINGS

Corresponding reference characters indicate corresponding parts throughout the drawings.

DETAILED DESCRIPTION OF THE INVENTION

Figure 1:
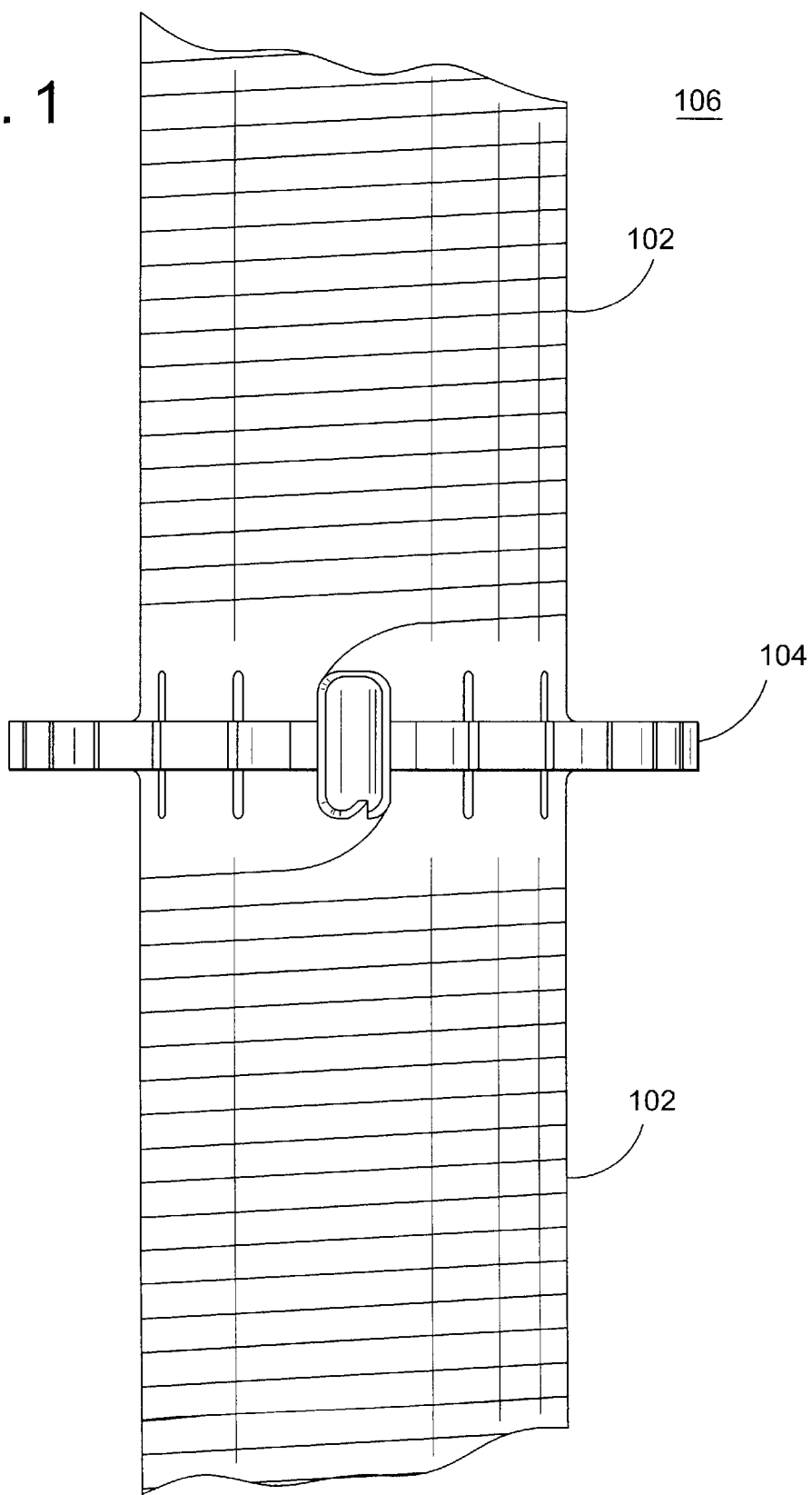
FIG. 1 is a perspective view of a split pair magnet according to one preferred embodiment of the invention.

Referring now to the drawings, a magnet according to the invention permits researchers to study aspects of many magnetic-field-induced phase transitions for the first time. For instance, the magnet can align the individual atoms of some materials so that neutron scattering reveals the detailed magnetic arrangement of a sample, in three dimensions, as the magnetic field is applied.

In one preferred embodiment, the repeating pulsed magnet applies a high magnetic field to a sample for diffraction and spectroscopic studies using a pulsed neutron source. In addition, the magnet may be used in connection with relaxational studies at steady-state sources. As illustrated in the accompanying figures, the magnet preferably has a gap of approximately 12.5 mm for the incident neutron beam to illuminate the sample. The novel design of the present invention permits observation of the neutrons scattered by the sample over large angles and does not limit observation to discrete beam holes or the like. Preferably, the magnet is energized by, for example, a pulsing circuit (see FIG. 7) such that it has a peak field of approximately 30 T and operates at a repetition frequency of approximately 2 Hz and a pulse length of approximately 4 ms. Advantageously, the magnet of the present invention has an operational life span of at least 10,000 repetitions and is designed for reliable operation for a life span on the order of 10 million repetitions.

Those skilled in the art recognize that neutron scattering experiments are limited by the available neutron flux. Pulsed spallation neutron sources, such as those located in the Los Alamos Neutron Science Center (LANSCE) and Japan's KEK National Labor (KENS), operate at repetition frequencies of, for example, 20 Hz. Unfortunately, presently available magnets are unable to match these frequencies while providing high magnetic fields and adequate operational life span. In this instance, the magnet of the present invention provides a shorter thermal path during continuous cooling (e.g., by water or liquid nitrogen), which is a factor in increasing the magnet pulse frequency from about 0.5 Hz known in the prior art to about 2 Hz. This increase means an increase in average power and water flow at the expense of space factor and cooling time. The magnet preferably pulses every tenth neutron pulse.

Referring now to FIG. 1, there is shown a perspective view of a split paired magnet according to one preferred embodiment of the invention. In general, the magnet is a coil 100 of conductive material. According to one embodiment, two outer body portions 102 of the coil 100 are made from high strength, high conductivity material such as a copper alloy and joined together by a mid-plane portion 104 made from, for example, high strength aluminum alloy. Preferably, the coil has a relatively coarse pitch to keep the voltage relatively low and the pulse length short. Pitch may vary between 2 mm and 7 mm per turn. As described below in more detail, it is to be understood that the magnet may be constructed from multiple layers.

Figure 2A:
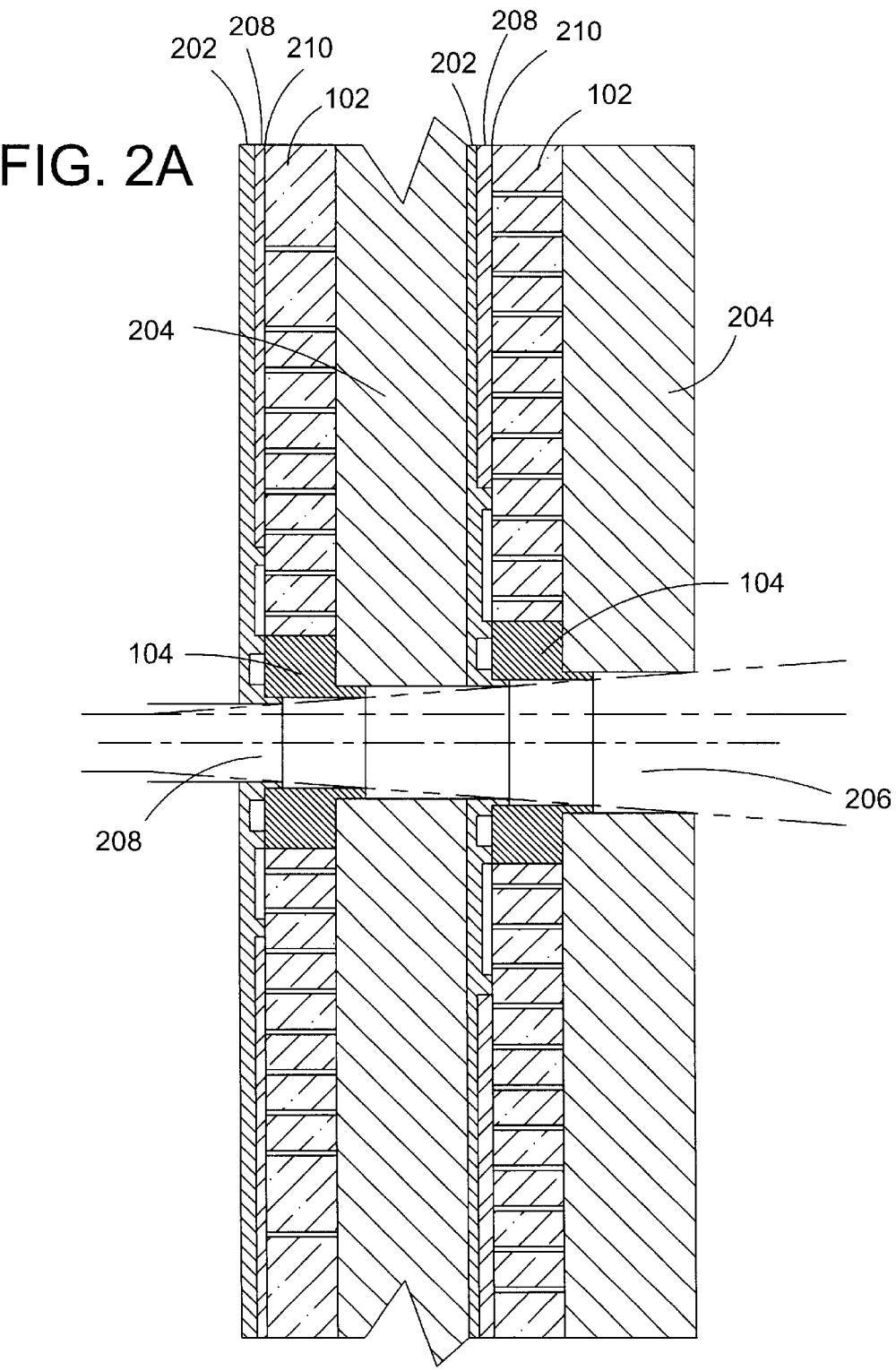
FIG. 2a is a vertical cross sectional view illustrating the construction of an exemplary multiple layer split paired magnet according to one preferred embodiment of the invention.

Referring next to FIG. 2a, a vertical cross sectional view illustrates the construction of an exemplary multiple layer split pair magnet according to one preferred embodiment of the invention. In this instance, two concentrically adjacent coils 100 form the multiple layer split paired magnet. One process for constructing the coil 100 involves welding two copper alloy bars to an aluminum alloy plate. The resulting bimetallic bar is cut into a helix using wire electro-discharge machining (EDM). The kerf of the helical structure is filled with an insulating material 202. The insulator needs to have high electrical and mechanical strength while operating underwater at temperatures as high as 100° C. Candidate materials include glass fibers and micro-spheres embedded in an epoxy matrix. An overbanding material 204 such as zylon-epoxy seals the outer portion of the helical structure (i.e. coil). Thus, as described above, in reference to FIG. 1, each coil 100 consist of two copper alloy outer portions 102 joined to an aluminum mid-plane portion 104.

The aluminum mid-plane portion 104 includes an opening 206, or gap, through which a high intensity neutron beam illuminates the target sample. In one embodiment, a quartz plug 208 fills the opening 206 in the aluminum mid-plane portion 104. The quartz plug 208 provides strength while also allowing the high intensity neutron beam to penetrate the opening 206 with little interference for illuminating the target sample.

At each end of the coil's inner diameter, supply lines 208 and return lines 210 direct a coolant such as water or liquid nitrogen, into and out of the coil for continuous cooling. The coolant is not permitted in the aluminum mid-plane portion 104 of the magnet. In this example, water enters at each end of the coil 100 through the supply lines 208 and flows toward the aluminum mid-plane portion of the coil 100. Prior to reaching the mid-plane the water flow is re-directed to each end of the coil 100 through return lines 210.

Figure 2B:
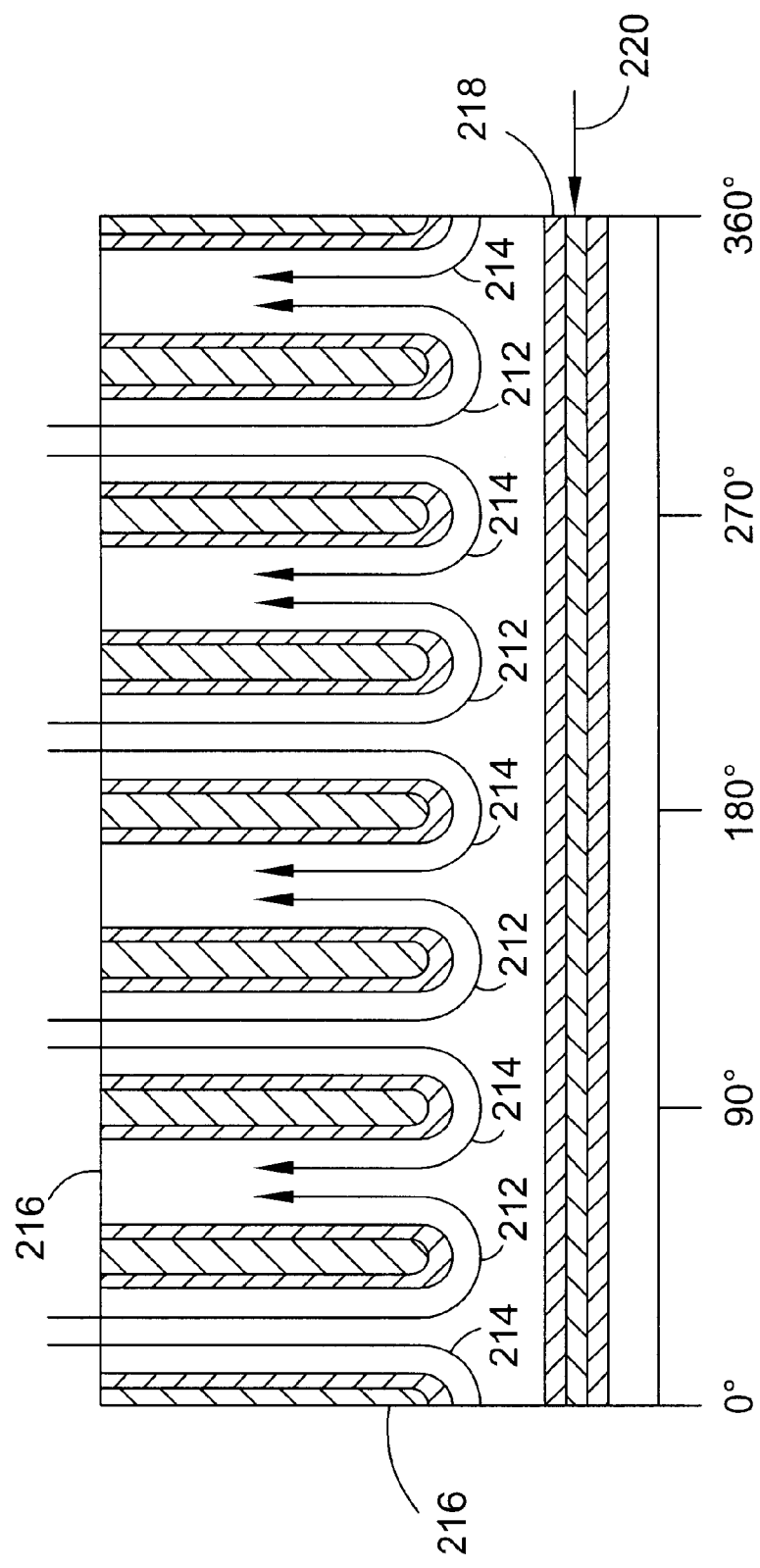
FIG. 2b is a vertical cross sectional view of an upper coil portion illustrating the flow of cooling water in more detail.

Referring next to FIG. 2b, a vertical cross sectional view of an upper coil portion illustrates the flow of cooling water in more detail. For simplicity, FIG. 2b illustrates an unrolled view of an upper coil portion. As indicated by arrows 212 and 214, the water enters at an end 216 of the coil 100 and flows toward the mid-plane indicated generally at reference character 218. In this instance, the water flow is re-directed by a rubber o-ring 220 positioned at the mid-plane portion 218 of the coil 100. As indicated by arrows 212 and 214, the water then flows from mid-plane 218 to the other end 216 of the coil 100.

Figure 3A:
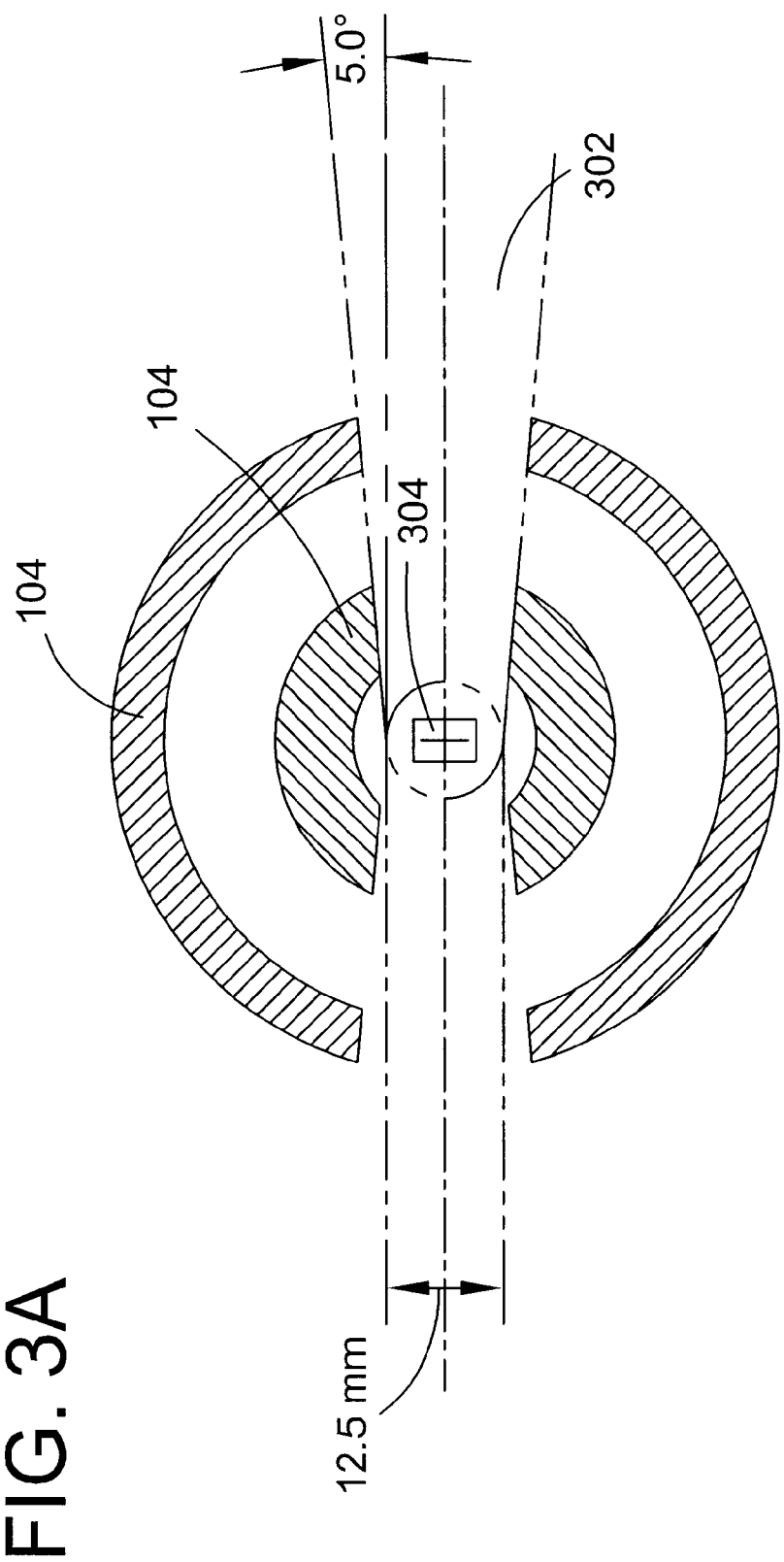
FIGS. 3a and 3b are horizontal cross sectional views illustrating openings in aluminum mid-plane portions of a coil.
Figure 3B:
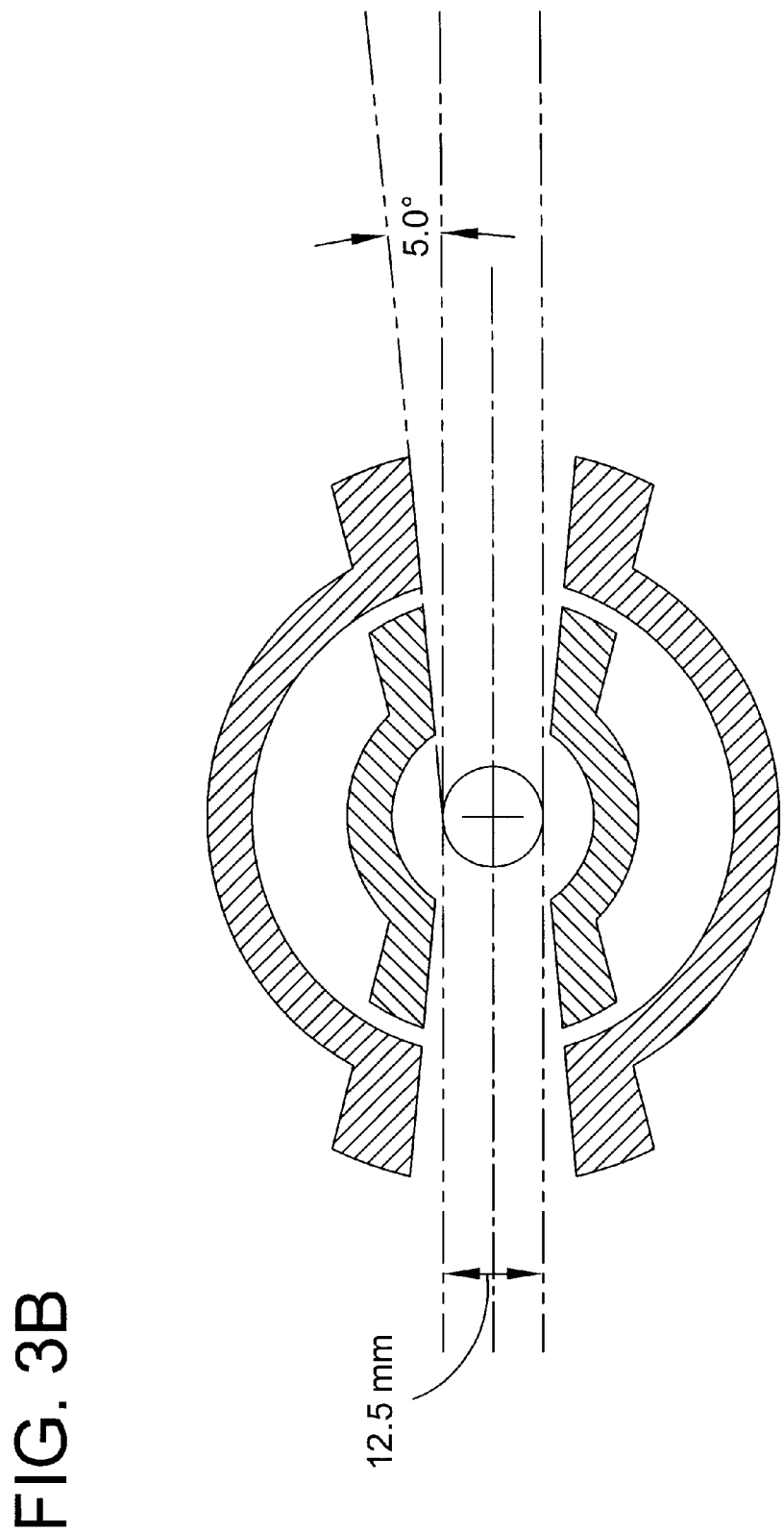

Referring next to FIGS. 3a and 3b, horizontal cross sectional views illustrate openings in aluminum mid-plane portions of a coil. The aluminum mid-plane section 104 of the coil 100 shown in FIG. 3a has a opening 302 that measures approximately 12.5 mm in width. The opening 302 extends through the entire mid-plane section 105. In operation, a neutron source (e.g., reactor or spallation) fires a high intensity incident beam through the opening 302 and illuminates a sample 304 positioned within the opening. The atomic structure of the sample 304 scatters some of the neutrons. Advantageously, the mid-plane material of the coil (e.g., aluminum) is selected so that it will have minimal interaction with the scattered neutrons. Because there is little interaction between the aluminum mid-plane and the scattering neutrons, the neutrons are allowed to scatter through 360 degrees. In this example, the actual openings in the aluminum structures of the mid plane section are flared and therefore greater than 12.5 mm. The flare creates a 5 degree angle with the tangent line of an 12.5 mm diameter circle centered within the mid-plane section. FIG. 3b is exemplary and illustrates an alternative shape of an aluminum mid-plane 104. In another embodiment, copper alloy is used for forming the coils and joining the coil portions in the gap.

Figure 3C:
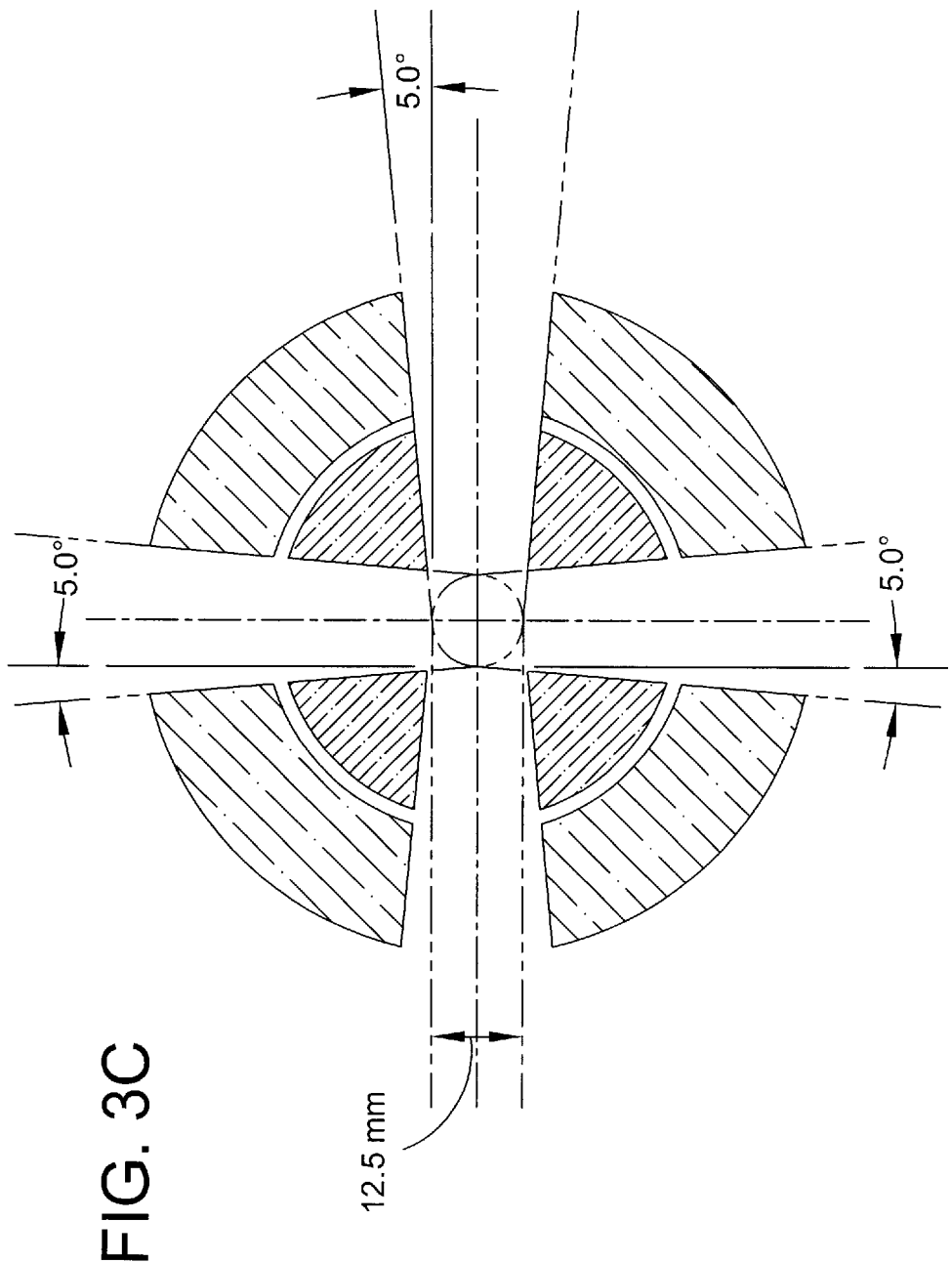
FIGS. 3c and 3d are horizontal cross sectional views illustrating openings in copper mid-plane portions of a coil.
Figure 3D:
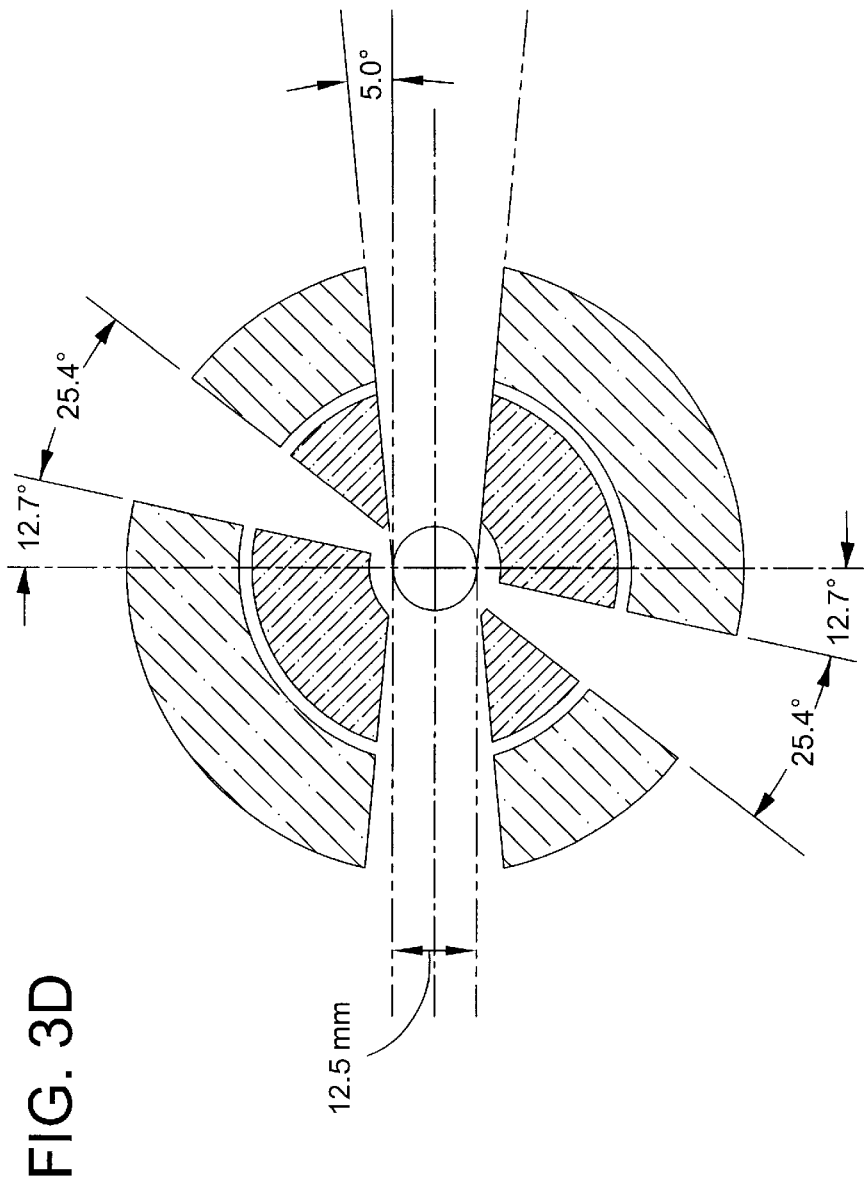

Referring now to FIGS. 3c and 3d, horizontal cross sectional views illustrate openings in copper mid-plane portions of a coil. These figures are exemplary and are shown to illustrate alternative materials and shapes for the mid-plane portion of the coil 100.

Figure 4:
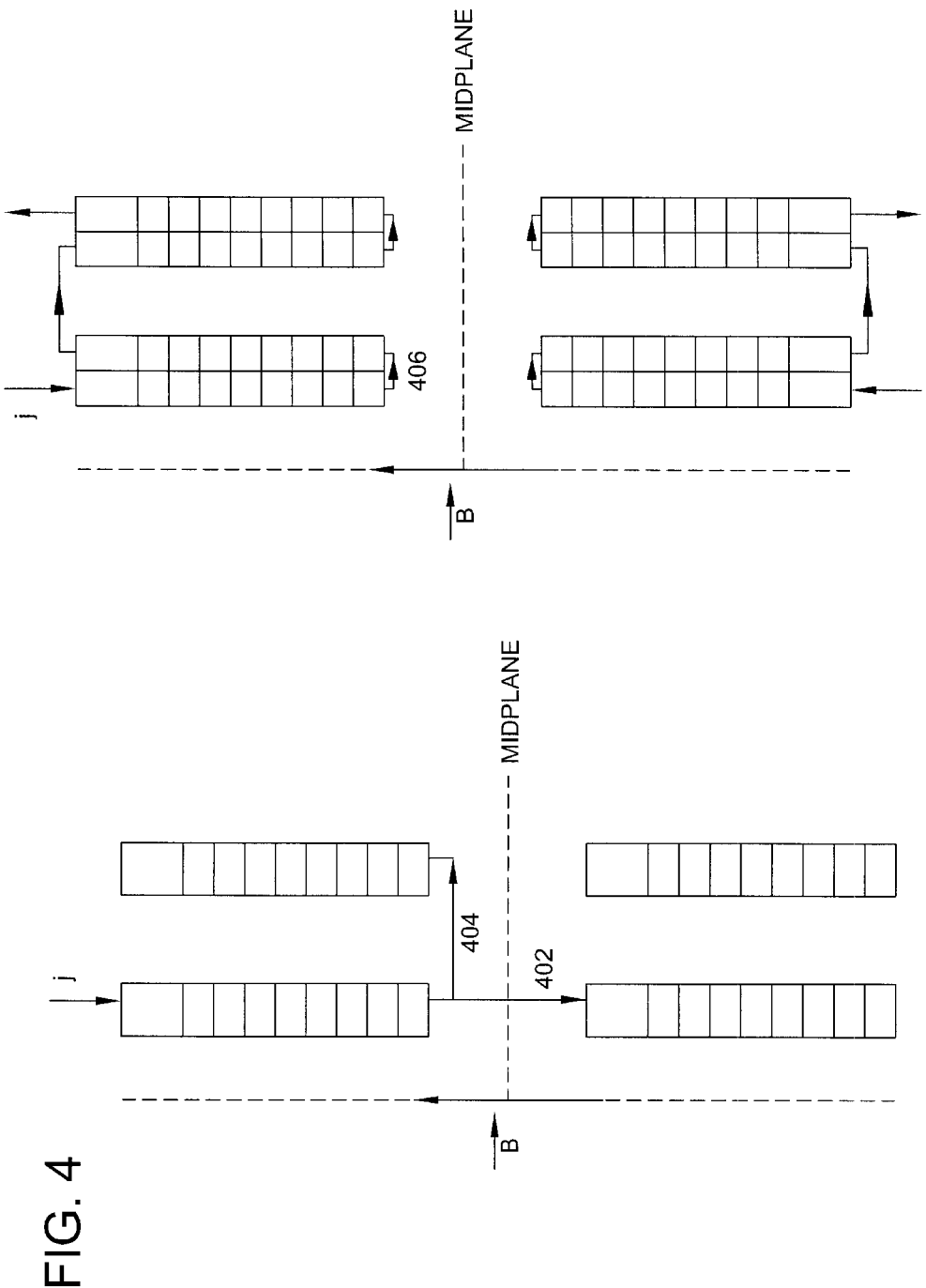
FIG. 4 is an exemplary schematic diagram illustrating three current paths in a two layer split paired magnet.

Referring next to FIG. 4, an exemplary schematic diagram illustrates three current paths, 402, 404, and 406, in a two layer split paired magnet. As described above, pulsed, high field magnets are subject to incredible stresses that make the fatigue lifetime of its components (i.e., conductors and insulation) an important consideration. According to the invention, the magnet has a conductive mid-plane forming a high strength, high conductivity joint. This permits current (e.g., 80 kA) to flow along path 402 in a preferred embodiment of the invention, which results in minimal Lorenz forces when compared to current flowing along path 404.

Figure 5:
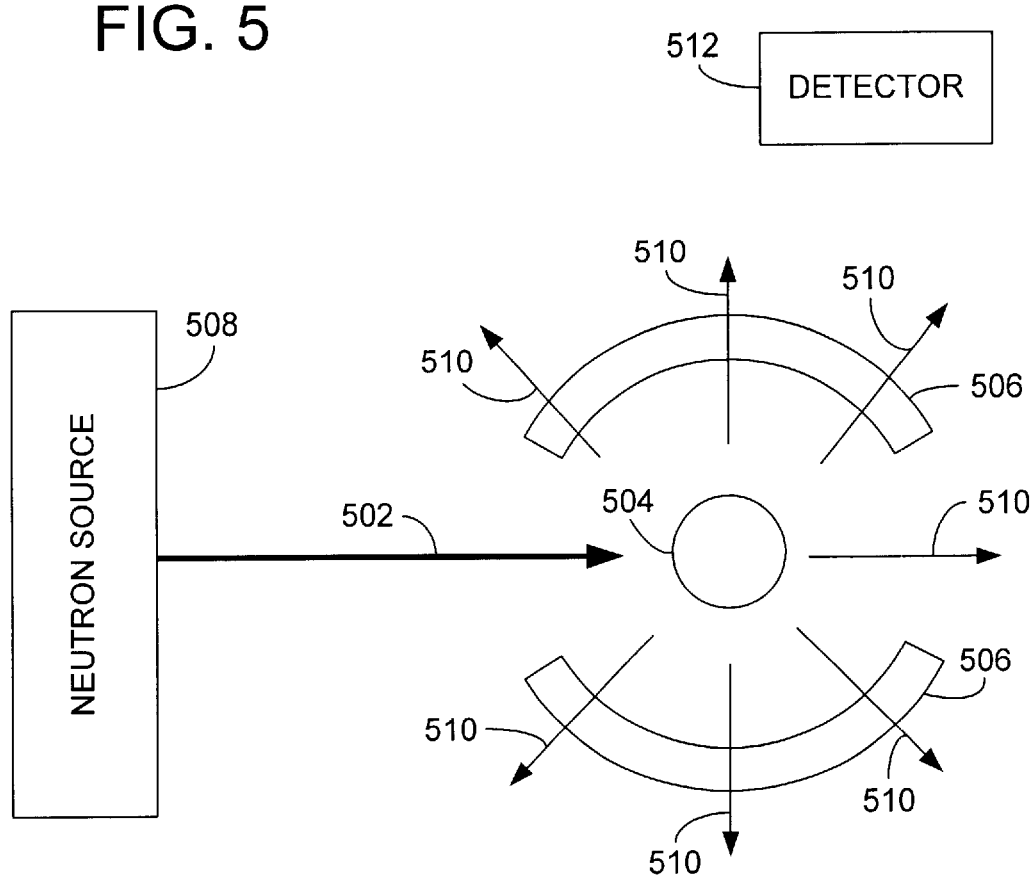
FIG. 5 is a horizontal cross sectional view illustrating neutron scattering resulting from a neutron beam illuminating a sample within the opening of a mid-plane portion of the coil.

Referring now to FIG. 5, a horizontal cross sectional view illustrates neutron scattering resulting from a neutron beam 502 illuminating a sample 504 within the opening of a mid-plane 506 of the coil 100. A pulsed neutron source 508 generates the neutron beam 502. The neutron source 508 is aligned such that the generated neutron beam is directed toward the sample 504. When the neutron source 508 is activated, the neutron beam penetrates the opening of the mid-plane 506 of the coil and illuminates the sample 504. As described in reference to FIGS. 3a and 3b, the atomic structure of the sample 504 scatters some of the neutrons. In this instance, the mid-plane 506 is constructed of aluminum and the scattering neutrons pass through the mid-plane 506 through 360 degrees, as indicated by arrows 510.

Figure 6:
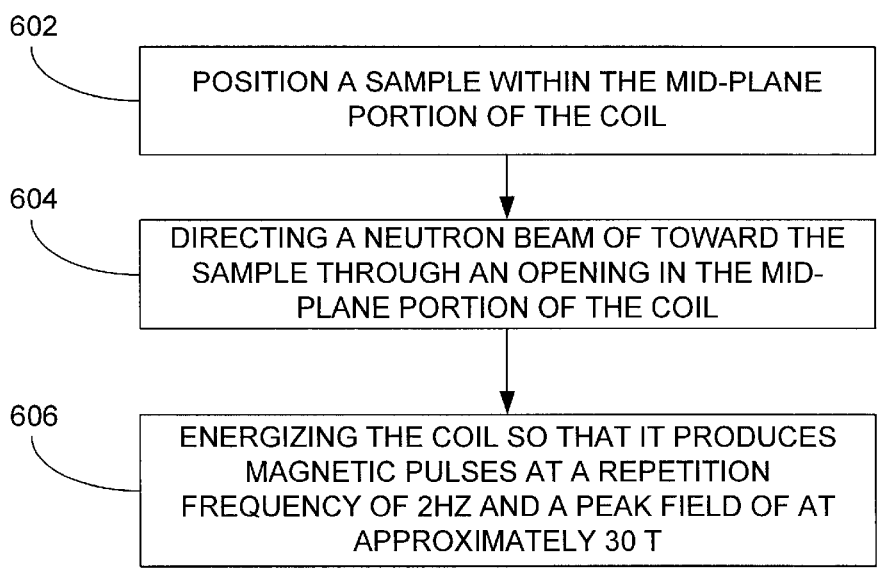
FIG. 6 is an exemplary flow chart illustrating a method for analyzing the atomic structure of a sample with a repeating pulsed magnet.

Referring next to FIG. 6, an exemplary flow chart illustrates a method for analyzing the atomic structure of a sample with a repeating pulsed magnet. At step 602, a sample is positioned within the mid-plane portion of a coil forming the magnet. A neutron beam is pulsed at a repetition frequency of approximately 20 Hz, and directed toward a sample positioned in the opening of the mid-plane portion of the coil at step 604. At step 606, the coil is energized such that when the magnet is operating it produces magnetic pulses at a repetition frequency of approximately 2 Hz, and a peak field of approximately 30 T.

Figure 7:
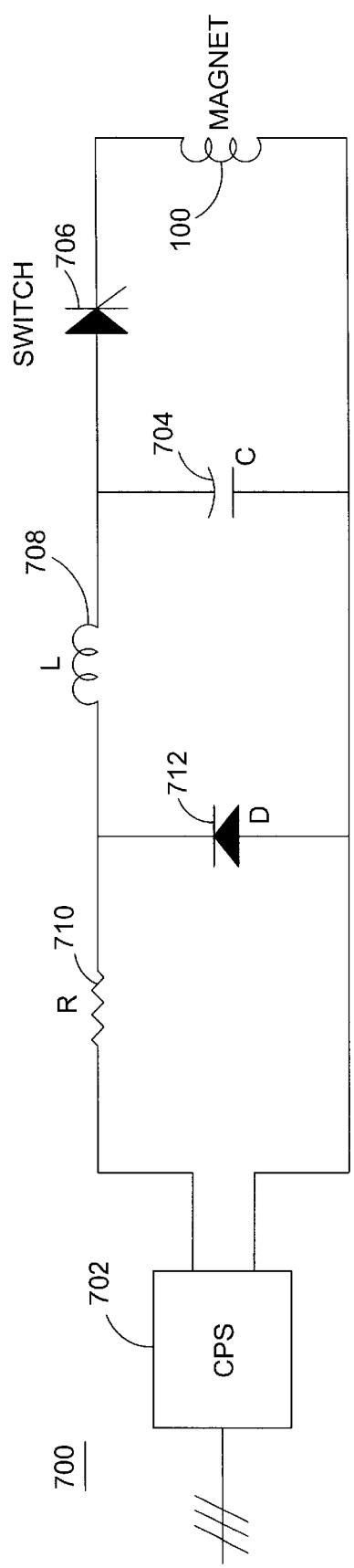
FIG. 7 is a schematic diagram of a pulsing circuit of the magnet system.

Referring next to FIG. 7, a schematic diagram of a pulsing circuit of the magnet system is shown. The pulsing circuit 700 is, for example, a double ringing circuit that is electrically connected to a magnet for generating a repetitive magnetic field. The pulsing circuit 700 includes a charging power supply 702 that supplies power (electrical energy) from the electrical grid and charges a capacitor 704. After the capacitor 704 is charged, an electronic thyristor switch 706 is closed allowing a high current to flow through the magnet which is represented by a combined inductance (i.e. inductor 708) and resistance (i.e. resistor 710). The current pulse is kept very short by proper selection of the magnet's resistance and inductance. When the current decays to zero (about 3–4 ms) the switch 704 opens. The capacitor 704 reverses polarity through the diode 712 and ringing inductor 708. At this point, the energy stored in the capacitor 704 is approximately 70% of its initial value and the charge has returned to its initial polarity. The charging power supply 702 is then used to return capacitor 704 to its initial charge prior to the next pulse. During the current pulse, an intense magnetic field is generated on the material sample by the magnet. The magnet will heat up as much as 100° C. during a 4 ms pulse. Cold water pumped through the magnet to return the temperature back to its original value prior to the next pulse.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A magnet for use with a neutron scattering apparatus, said neutron scattering apparatus providing an incident beam of neutrons to a sample under analysis, said magnet comprising a conductive coil, said coil having first and second body portions of high conductivity material and having a mid-plane portion therebetween in which the sample under analysis is positioned, said first and second body portions of the coil being electrically connected to each other via the mid-plane portion of the coil between the body portions of the coil, said mid-plane portion of the coil being a conductive material substantially non-interactive with neutrons.

2. The magnet of claim 1 wherein the magnet is a high field repeating pulsed magnet.

3. The magnet of claim 1 wherein current flows in the first body portion of the coil, through the mid-plane portion of the coil, and then in the second body portion of the coil.

4. The magnet of claim 1 wherein the body portions of the coil are a copper-based conductive material.

5. The magnet of claim 1 wherein the mid-plane portion of the coil is an aluminum-based conductive material.

6. The magnet of claim 1 wherein the mid-plane portion of the coil has an opening therethrough defining a path for the incident beam of neutrons provided by the neutron scattering apparatus and wherein the sample under analysis is positioned in the mid-plane portion of the coil in the path of the incident beam of neutrons.

7. The magnet of claim 6 wherein the neutrons in the incident beam that are scattered by the sample under analysis substantially pass through the conductive material of mid-plane portion of the coil.

8. The magnet of claim 1 wherein the mid-plane portion of the coil is welded to the body portions of the coil.

9. The magnet of claim 1 wherein the body portions of the coil comprise multiple layers of conductive material.

10. The magnet of claim 1 wherein the coil, when energized, is operable to generate a peak field of at least approximately 30 T.

11. The magnet of claim 1 wherein the coil, when energized, is operable to produce magnetic pulses at a repetition frequency of at least approximately 2 Hz.

12. The magnet of claim 1 wherein the coil, when energized, is operable to produce magnetic pulses each having a pulse length of at least approximately 4 ms.

13. The magnet of claim 1 wherein the coil, when energized, has an operational life span of substantially greater than approximately 10,000 pulse repetitions.

14. A method for analyzing the atomic structure of a sample with a repeating pulsed magnetic field, said method comprising:

positioning the sample within a mid-plane portion of a conductive coil, wherein said coil includes first and second body portions of high conductivity material electrically connected to each other via said mid-plane portion;

directing a neutron beam through an opening in the mid-plane portion of the conductive coil and toward said positioned sample;

energizing the coil to produce magnetic pulses at a repetition frequency of at least approximately 2 Hz and a peak field of at least approximately 30 T when the magnet is operating.

15. The method of claim 14 further comprising pulsing the neutron beam at a repetition frequency of at least approximately 20 Hz.

16. The method of claim 14 wherein the neutrons scattered by the sample under analysis substantially pass through the conductive material of the mid-plane portion of the coil.

17. The method of claim 14 wherein the body portions of the coil are a copper-based conductive material.

18. The method of claim 14 wherein the mid-plane portion of the coil is an aluminum-based conductive material.

19. The method of claim 14 wherein energizing the coil includes causing current flow in the first body portion of the coil, through the mid-plane portion of the coil, and then in the second body portion of the coil.

20. The method of claim 14 wherein the mid-plane portion of the coil comprises a conductive material substantially non-interactive with neutrons.

21. The method of claim 14 wherein energizing the coil includes energizing the coil to produce magnetic pulses each having a pulse length of at least approximately 4 ms.

* * * * *